(12) United States Patent
Di Berardino et al.

(10) Patent No.: US 9,372,183 B2
(45) Date of Patent: Jun. 21, 2016

(54) METHOD AND APPARATUS FOR THE DISCRIMINATION OF THE CELL LOAD IN MILK

(71) Applicant: Amphasys AG, Root Laengenbold (CH)

(72) Inventors: Marco Di Berardino, Rain (CH); Grit Schade-Kampmann, Muhlau (CH)

(73) Assignee: Amphasys AG, Root Laengenbold (CH)

( * ) Notice: Subject to any disclaimer, the term of this patent is extended or adjusted under 35 U.S.C. 154(b) by 4 days.

(21) Appl. No.: 14/580,524

(22) Filed: Dec. 23, 2014

(65) Prior Publication Data

US 2015/0253302 A1     Sep. 10, 2015

(30) Foreign Application Priority Data

Mar. 5, 2014   (EP) ..................................... 14157928

(51) Int. Cl.
   *G01N 33/04*     (2006.01)
   *G01N 33/487*    (2006.01)
   *A01J 5/013*     (2006.01)
   *G01N 15/10*     (2006.01)

(52) U.S. Cl.
   CPC ......... *G01N 33/48735* (2013.01); *A01J 5/0132* (2013.01); *A01J 5/0133* (2013.01); *G01N 15/1031* (2013.01); *G01N 15/1056* (2013.01); *G01N 33/04* (2013.01); *G01N 33/48785* (2013.01)

(58) Field of Classification Search
   None
   See application file for complete search history.

(56) References Cited

U.S. PATENT DOCUMENTS

2012/0310541 A1   12/2012 Katz et al.

OTHER PUBLICATIONS

Hunt et al., Characterization of the Diversity and Temporal Stability of Bacterial Communities in Human Milk, PLoS One 6(6), Jun. 17, 2011.*
Pierzchalski et al., "Label-Free Hybridoma Cell Culture Quality Control by a Chip-Based Impedance Flow Cytometer", Lab Chip (2012), 12 (21), pp. 4533-4545.
European Search Report for corresponding European Application No. EP 14 15 7928 dated Jul. 4, 2014.
K. L. Smith, "Standards for Somatic Cells in Milk: Physiological and Regulatory", International Dairy Federation Mastitis Newsletter, Sep. 1996, p. 7.
Schalm & Norlander, "Experiments and Observations Leading to Development of the California Mastitis Test", Journal of the American Veterinary Medical Association, 1957, pp. 130, 199-204.
Grenvall et al., "Label-Free Somatic Cell Cytometry in Raw Milk Using Acustophoresis", Cytometry A. published online Oct. 18, 2012.
Schade-Kampmann et al., "On-Chip Non-Invasive and Label-Free Cell Discrimination by Impedance Spectroscopy", Cell Prolif. 2008, pp. 41, 830-840.
David et al., "Viability and Membrane Potential Analysis of Bacillus Megaterium Cells by Impedance Flow Cytometer", Biotechnology & Bioengineering (2012), 109 (2), pp. 883-492.
Cheung et al., "Impedance Spectroscopy Flow Cytometer: On-Chip Label-Free Cell Differentiation", Cytometry A (2005), 65A, pp. 124-132.
James et al., "Impedimetric and Optical Interrogation of Single Cells in a Microfluidic Device for Real-Time Viability and Chemical Response Assessment", Biosensors and Bioelectronics (2008), 23, pp. 845-851.
Arkadiusz Pierzchalski et al: "Label-free single cell analysis with a chip-based impedance flow cytometer", Proceedings of SPIE, vol. 7568, 75681B, Feb. 11, 2010, pp. 1-11, XP055060411.
Tao Sun et al: Digital signal processing methods for impedance microfluidic cytometry, Microfluidics and Nanofluidics, Springer, Berlin, DE, vol. 6, No. 2, Jun. 14, 2008, pp. 179-187, XP019667781.
Harris C. M. et al: 'Dielectric permittivity of microbial suspensions at radio frequencies: a novel method for the real-time estimation of microbial biomass', Enzyme and Microbial Technology, Stoneham, MA, US, vol. 9, No. 3, Mar. 2, 1987, pp. 181-186, XP023689236.

\* cited by examiner

*Primary Examiner* — Suzanne M Noakes
*Assistant Examiner* — Stephen Chong
(74) *Attorney, Agent, or Firm* — Renner, Otto, Boisselle & Sklar, LLP

(57) ABSTRACT

A method is provided for the discrimination of cells from other particles, as well as of different types of cells in raw milk samples by impedance microflow cytometry. A method is provided of analysing the quality of raw milk in terms of its bacterial and somatic cell content without the need to pretreat the milk sample, such that the analysis can take place directly at the production site. One advantage is discriminating and counting somatic cells from milk particles (consisting mainly of lipid vesicles) by high-frequency impedance analysis directly performed on untreated raw milk. Another advantage is that the method allows diagnosing the status of a mastitis infection directly after milking according to the analysis of the somatic cell count. Another advantage is to allow a fast method for determining the bacterial cell count in raw milk directly after milking. In addition, viability of both somatic and bacterial cells can be determined without the need of any cell label. A further advantage is, that the analysis can be obtained in real-time, directly after the raw milk has passed the micro channel of the microfluidic device.

5 Claims, 7 Drawing Sheets

I ... Lymphocytes
II ... Granulocytes (neutrophils)
III ... Monocytes/Macrophages

METHOD AND APPARATUS FOR THE DISCRIMINATION OF THE CELL LOAD IN MILK

CROSS-REFERENCE TO RELATED APPLICATION

The present application claims priority under 35 USC §119 to European Patent Application No. 14 157 928.4, filed Mar. 5, 2014, the entire disclosure of which is incorporated herein by reference.

TECHNICAL FIELD OF THE INVENTION

The present invention refers to a method for the discrimination of cells from other particles, as well as of different types of cells in raw milk samples by impedance microflow cytometry.

DESCRIPTION OF THE RELATED ART

Among many parameters defining the quality of milk, bacterial (BCC) and somatic cell counts (SCC) are of outmost importance, since they significantly affect the quality of the deriving milk products, but also provide information about the health status of the cows.

Somatic cells are white blood cells known as leukocytes (lymphocytes, granulocytes, monocytes and macrophages) and originate from the animal's udder. The number of these cells can increase in response to bacterial infections, which can cause mastitis. Normally, milk of uninfected cows has less than 100,000 cells/ml, values higher than 300,000 cells/ml indicate infected cows, while values of more than 1,000,000 cells/ml are typical for sick cows. The threshold value for human consumption or for further processing into food products for human consumption is below 400,000 cells/ml in Europe, but can be higher in the US. Generally, cows with SCC higher than 300,000 cells/ml are regarded as infected (Smith, K. L., in STANDARDS FOR SOMATIC CELLS IN MILK: PHYSIOLOGICAL AND REGULATORY (1996), International Dairy Federation Mastitis Newsletter, September, p. 7). In order to rate the milk quality, consequently, a reliable and precise somatic cell counting method is mandatory. The simple and often used cow-side California mastitis test (also called Schalm-Test according to its inventors Schalm & Norlander in EXPERIMENTS AND OBSERVATIONS LEADING TO DEVELOPMENT OF THE CALIFORNIA MASTITIS TEST, Journal of the American Veterinary Medical Association (1957): 130,199-204) is an indirect, qualitative method and does not provide such detailed information to qualify the milk quality for human consumption.

Generally, SCC measurements are performed daily on pooled milk from many animals at the dairy product manufacturer's laboratory after unloading the milk truck, and not from individual cows. The main reason is because testing of individual animals at each milking would be too expensive. This also means that milk from a sick cow is diluted and averaged down by the healthy animals. Thus, sick animals might remain undetected or discovered to be sick in a later stage, without affecting the overall milk quality rating. Moreover, since also the milk of several farmers is pooled, farmers are compensated for the average rating of the milk load. Dairy product manufacturers, however, would rather prefer to compensate each farmer according to the daily delivered quality of his milk, which is currently not feasible. The expensive analyses relate mainly to the currently available technologies, which are either based on optical or electrical measurements. Optical measurements need first the cells to be labelled before the analysis, which therefore usually requires costly chemical reagents or disposables. Electrical measurements, on the other hand, are based on an impedance analysis, with which, however, other non-cellular milk particles interfere and must be removed by several centrifugation steps. These devices can therefore not be used at the farmer's site. Thus, many efforts are undertaken in order to simplify analysis methods and reduce analysis costs. Label-free technologies are preferred methods, since these normally do not require reagents and disposables and concurrently simplify sample preparation procedures. The electrical tools used so far are so-called Coulter counters, which can count cells and discriminate them by size. Since raw milk contains many particles, mainly fat vesicles with a size similar to the leukocytes (5-10 µm), reliable cell counting is not possible because these particles easily outnumber the somatic cells and therefore severely interfere with the measurement. Consequently, these particles must be separated from somatic cells prior to the measurement. This is achieved either by centrifugation, in which the cells are sedimented and fat vesicles removed from the supernatant, or, as recently shown by Grenvall et al., in LABEL-FREE SOMATIC CELL CYTOMETRY IN RAW MILK USING ACUSTOPHORESIS (2012), Cytometry A, published online Oct. 18, 2012, using acoustic wave technology for separating fat vesicles from somatic cells. While centrifugation usually requires a laboratory infrastructure, acustophoresis seems more promising, but also complicates the Coulter counter technology any further.

Conventional Coulter counters measure the impedance using direct current (DC) or low frequency alternate current (AC, max. 1 kHz), allowing for reliable cell counting and cell size discrimination. This technology has been improved in the last decade through the advent of micro technologies. EP 1 335 198 B1 discloses a micro fluidic approach with an electrode arrangement that permits impedance analysis of cells over a broad frequency range (100 kHz-20 MHz). High frequency analyses go beyond simple cell counting and sizing and interrogate the dielectric properties of cells, which allow for cell discrimination in various applications, such as cell differentiation shown in Schade-Kampmann et al. titled ON-CHIP NON-INVASIVE AND LABEL-FREE CELL DISCRIMINATION BY IMPEDANCE SPECTROSCOPY, Cell Prolif. (2008), 41, 830-840, or animal and bacterial cell viability described in Pierzchalski et al. titled LABEL-FREE HYBRIDOMA CELL CULTURE QUALITY CONTROL BY A CHIP-BASED IMPEDANCE FLOW CYTOMETER, Lab Chip (2012), 12 (21), 4533-4543 and in David et al. titled VIABILITY AND MEMBRANE POTENTIAL ANALYSIS OF *BACILLUS MEGATERIUM* CELLS BY IMPEDANCE FLOW CYTOMETRY, Biotechnology & Bioengineering (2012), 109 (2), 883-492, respectively. In contrast to conventional Coulter counter measurements, in which the signal amplitude is used for counting and sizing cells, high-frequency analyses provide additional information, even if the cells have the same dimensions. Such analyses, however, have been only performed in a laboratory environment with cells suspended in well-defined media.

An approach for analysing various cell parameters in milk using impedance analysis over a huge frequency range (0.3 MHz-1.4 GHz) has been disclosed in Patent US 2012/0310541 A1. Impedance measurements on milk at various frequencies over a radiofrequency range between 100 MHz and 2 GHz can provide indications about somatic cell concentrations, but at a rather qualitative level, since the analysis is not performed at the single cell level. This method is not sensitive enough to determine SSC in such a way that it can be used for rating the milk quality.

It is expected that milk particles (lipid vesicles) and somatic cells behave differently in terms of the dielectric properties of their cell interior, as predicted by Cheung et al. in IMPEDANCE SPECTROSCOPY FLOW CYTOMETRY: ON-CHIP LABEL-FREE CELL DIFFERENTIATION, Cytometry A (2005), 65A, 124-132.

Impedance analysis on single cells in a frequency range up to 0.1 MHz has been shown to allow for splitting the amplitude and phase angle components and to permit the discrimination of cells from non-cellular particles as well as discrimination of live/dead cells (Conrad et al. in IMPEDIMETRIC AND OPTICAL INTERROGATION OF SINGLE CELLS IN A MICROFLUIDIC DEVICE FOR REAL-TIME VIABILITY AND CHEMICAL RESPONSE ASSESSMENT, Biosensors and Bioelecrtronics (2008), 23, 845-851). The device used for this analysis, however, is trapping single cells prior to measuring the impedance signal and thus not suitable neither for cell density determination nor for the analyisis of thousands of cells in a short period of time. Moreover, even though non-cellular particles (polystyrene beads) can be discriminated from cells, a much higher frequency is required to do the same with milk particles, since these fat globules behave much more similar to cells when exposed to an electric field than polystyrene beads.

SUMMARY OF THE INVENTION

The object of the present invention is therefore to propose a simple and fast method and apparatus for analysing milk, and more precisely, for discriminating cells from lipid vesicles and enumerating them in the accuracy needed for milk quality control applications in the dairy industry and at milk production sites.

This problem is solved by the invention having the features described herein.

According to a the method for the automatic discrimination and enumeration of particles, such as cells or fat globules, in milk of any animal, using high-frequency impedance measurements in a range between 0.1 and 30 MHz in a micro fluidic device, comprises:
  passing of raw milk through a filter to avoid clocking of the micro fluidic device;
  determining the impedance value of the milk and calibrating the micro fluidic device on said impedance value, if necessary;
  counting the particles and measuring the impedance of the particles;
  determining from one of the measured impedance components a trigger level suitable for noise extraction and particle recognition, respectively;
  determining from one impedance component a trigger level for discrimination of cells from non-cellular milk particles;
  analysing the impedance values depending on the amplitude values and the phase angle values; and
  discriminating and enumerating the cells and/or non-cellular milk particles according their amplitude and/or phase angle values.

According to the method raw milk is passed first through a filter with a mesh size of 15-30 µm and then directly through a micro fluidic chip with channel dimensions around 20 to 40 µm, which is slightly larger than the normal size of somatic cells (6-18 µm), containing microelectrodes that generate a high-frequency AC field (100 kHz-30 MHz). The impedance signal of raw milk as well as the impedance change caused by every single somatic cell and lipid vesicle crossing the established AC field is measured. About 1,000 to 10,000 cells/particles per second are analysed and about 10 to 100 µl are required per analysis, which takes less than one minute. It is important, that the method is performed by using raw milk, directly delivered from the animal. The analysis of the milk can be performed off-line or in the milk stream and the result of the analysis is delivered in real-time. No special sample preparation and thus time consuming measures are necessary.

Further, the impedance value of the milk is determined and the micro fluidic device on said impedance value, if necessary, is calibrated. Impedance analysis of cells or particles in a fluid usually depends on the dielectric properties of the cells on the one hand, but, on the other hand, also on the electric properties (conductivity) of the fluid. Normally, the impedance signal of a cell is determined by subtracting it from the impedance signal of the fluid. However, the fluid impedance influences signal amplitude and phase of the cell impedance. So, the same somatic or bacterial cell suspended in milk generates a different impedance change in milk with different intrinsic impedance values. For single analyses this is not an issue, since these values are analysed on a scatter plot and discrimination patterns set manually. For routine applications, such as cow-site milk analysis, automated and simple procedures are of outmost importance. Variable impedance values of milk, however, complicate an automated analysis, since the discrimination patterns must be adapted accordingly. Therefore, prior to cell analysis, the impedance of the milk is determined and the chip calibrated such that the subsequent analysis of the cells occurs under standardised conditions. This way the impedance values of the cells behave the same and identical discrimination patterns can be used for different milk samples. Moreover, there is a correlation between the SSC and the impedance value of the raw milk, such that the fluid impedance or the extend of the required calibration can be used as an early indicator of the SCC, which therefore has a similar information content as the Schalm test described above.

Next, the particles are counted and the impedance of the particles is measured. When raw milk passes through the micro fluidic chip every single particle is detected by impedance analysis and its impedance signal recorded. Enumeration (counting) of these cells provides on the one hand information about the cell content, and has on the other hand also the potential to assess the fat content of the milk. A precise analysis heavily depends on the choice of an appropriate trigger parameter, which is normally composed of one of the measured impedance components (real or imaginary parts, amplitude and phase angle) and its value (=trigger level). This allows for a selective distinction between milk particles or cells and the noise signals arising from a highly sensitive detection system. Only signals meeting the trigger parameters are recorded and are thus available for detailed analysis, which can occur either immediately after data acquisition or later using separate software tools. Triggering with a certain parameter, however, does not mean that only the triggering value is recorded. On the contrary, the complete information of every single particle or cell being recognised as such through the adjusted trigger is recorded comprising all components of the impedance signal.

A trigger parameter for noise extraction and particle recognition, respectively, and a trigger parameter for discrimination of cells from non-cellular milk particles are determined. Conventional Coulter counters, for example, simply measure a current pulse or voltage pulse caused by a particle that disturbs the applied electric field. The pulse height is proportional to the cell volume and used to analyse the particle size distribution. The distinction between particles and noise occurs by setting an appropriate pulse trigger value. Impedance is a complex quantity that consists of a real (R) and an imaginary part (I), but so far, the impedance signal was never split into its components for cell analysis in milk. The reason of that is the fact that for DC and low frequency measurements the imaginary part is either non-existent or irrelevant, respectively. In high-frequency measurements, however, these values become important and both real and imaginary part can be used as trigger parameters for extracting the particle signal from the noise as well as for discriminating particles with differences in these values from each other. This permits a simple and full characterisation of the particle population. In addition to these values, the amplitude (A, absolute value of real and imaginary part) alone or in combination with the phase angle ($\phi$, resulting from real and imaginary part), or any formula composed of these values (R, I, A, and $\phi$) can also be used as trigger parameters, permitting more selective discriminations between large and small cells, non-cellular milk particles and cells, as well as between dead and living cells of the same type. Besides the above mentioned trigger parameters also the trigger frequency can be varied. Normally, the trigger frequency is one of the selected measuring frequencies. Depending on the information to be obtained from raw milk analysis, therefore, the possibility to choose among various trigger parameters can simplify and possibly automate the read-out. Thus, for example, triggering with the amplitude will be selective for particle size and provide information about the size distribution of the particle population, while combining the trigger amplitude with a specific phase angle value can easily record either non-cellular milk particles or cells. Consequently, applying a specific trigger can provide a means of preselecting particles with particular properties and improve the performance of the micro fluidic system. For example, milk particles normally exceed by far the number of cells in raw milk. If one of these particles and a cell are simultaneously located in the detection area, the cell signal will be significantly influenced and either rejected as unusable or recorded for later analysis. For milk with high cell concentrations (>$10^6$ cells/ml) this can lead to the rejection of many cells and thus to inaccurate cell counts. The possibility to trigger with an appropriate phase value makes milk particles basically invisible to the system and reduces significantly the rejection rate. Moreover, more particles or cells can be recorded and analysed per time frame (or liquid volume), if only a part of them are detected through the trigger settings.

Another measure is analysing the impedance values depending on the amplitude values and the phase angle values. The absolute amplitude of the impedance signal is the main indicator of the cell dimension. This applies over a broad frequency range and extends to frequencies above 20 MHz. Other cellular parameters, such as membrane capacitance and cytoplasmic conductivity are expressed better through the phase angle value. At frequencies around 10 MHz the differences in the conductivity of the cell or particle interior as well as the composition of the outer membranes provide a means of discrimination for these particles if the phase value is considered. The method also permits the impedance measurement of the particles at different frequencies, which thus allows for interrogating size, membrane capacitance and cytoplasmic conductivity simultaneously, and provides relevant information about the physiological status of the analysed cells.

At least, the cells and/or non-cellular milk particles are selected according to their amplitude and/or phase angle values. After recording the particles and/or cells according to the adjusted trigger parameters, a detailed analysis can be performed by plotting the data on graphs representing the various impedance components and gating emerging cell populations against their impedance values, which can be simply R-, I-, A- and $\phi$-values, as well as more complex functions (polynomial gates for example).

The methods can be implemented on a chip (for example as disclosed in EP 1 335 198 B1) comprising the required measurement channel with the electrodes and the necessary positioning of the particles in the measurement channel. Such a chip can discriminate single cells from non-cellular milk particles according to the different dielectric properties. In addition, integration of specific trigger parameters can simplify cell discrimination and provide the required automation possibilities needed for a routine-based analysis. The chip may be used either by determining the difference between two impedance measurements of two electrodes pairs through which the particles pass or by measuring the impedance between only one electrode pair. A respective apparatus therefore comprises a micro fluidic device having an inlet and an outlet and a micro channel in between, with upper and lower electrodes in the micro channel forming a detection volume between the electrodes for milk particles passing through it; electrical means for connecting the electrodes with control means for generating an high frequency AC electric field between the electrodes and measuring the impedance between the electrodes with and without particles between the electrodes; input and monitoring means; means being adapted to determine the impedance value of the milk and to calibrate the micro fluidic device on said impedance value, if necessary; means being adapted to count the particles and measure the impedance of the particles; means to determine a trigger parameter for noise extraction and particle recognition, respectively; means being adapted to determine a trigger parameter for discrimination of cells from non-cellular milk particles; means being adapted to analyse the impedance values depending on the amplitude values and the phase angle values; and means being adapted to select the cells and/or non-cellular milk particles according their amplitude and/or phase angle values.

Since impedance flow cytometry is a label-free technology and milk does not need any pre-treatment prior to analysis, these methods can also occur in real time, if for example the technology is combined with automated milking devices. Moreover, as dairy milk manufacturers envisage compensating farmers individually according to the delivered milk quality, real-time information could be sent via mobile technology directly to the dairy facility.

One advantage of the invention is discriminating and counting somatic cells from milk particles (consisting mainly of lipid vesicles) by high-frequency impedance analysis directly performed on untreated raw milk. Another advantage of this invention is that the method allows diagnosing the status of a mastitis infection directly after milking according to the analysis of the SCC. Another advantage of this invention is to allow a fast method for determining the BCC in raw milk directly after milking. In addition, viability of both somatic and bacterial cells can be determined without the need of any cell label. A further advantage is that the analysis can be obtained in real-time, directly after the raw milk has passed the micro channel.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

Figure 1:
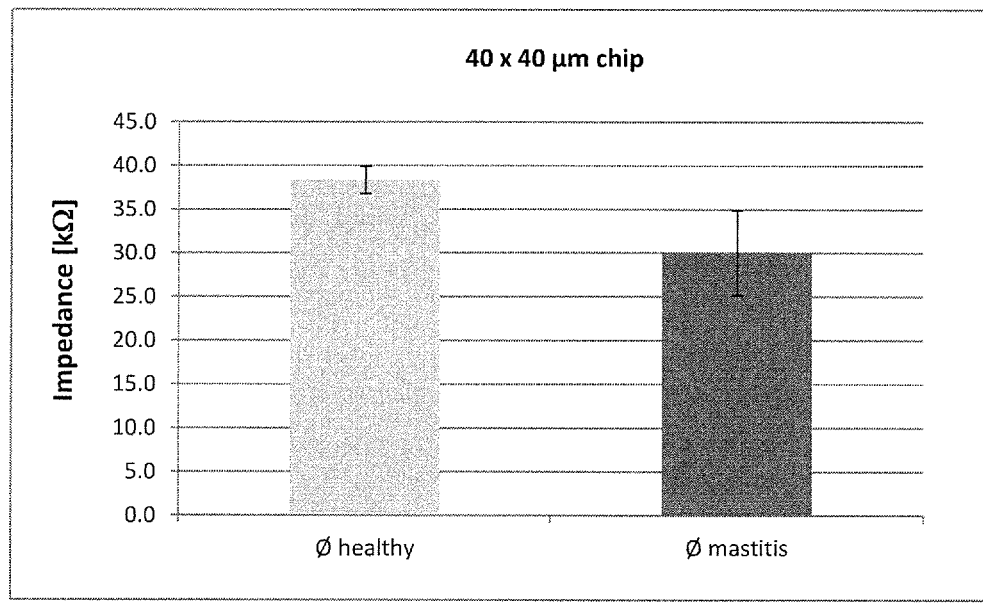
FIG. 1 summarizes the results obtained from the analysis of raw milk deriving from 14 cows, 6 of which had more than 400,000 cells/ml. Impedance analysis of raw milk.

The analysis according to FIG. 1 was performed with a chip with 40×40 μm sensing channel dimensions. Bright bar represent healthy, dark bar infected samples. The histograms show the mean values and standard deviations of the absolute impedance amplitudes in kΩ, which depend on the channel dimensions. The figure shows that the impedance values of raw milk with higher SCCs have lower impedance amplitudes. Thus, low impedance values of raw milk provide first qualitative indications of increased somatic cell count.

Figure 2:
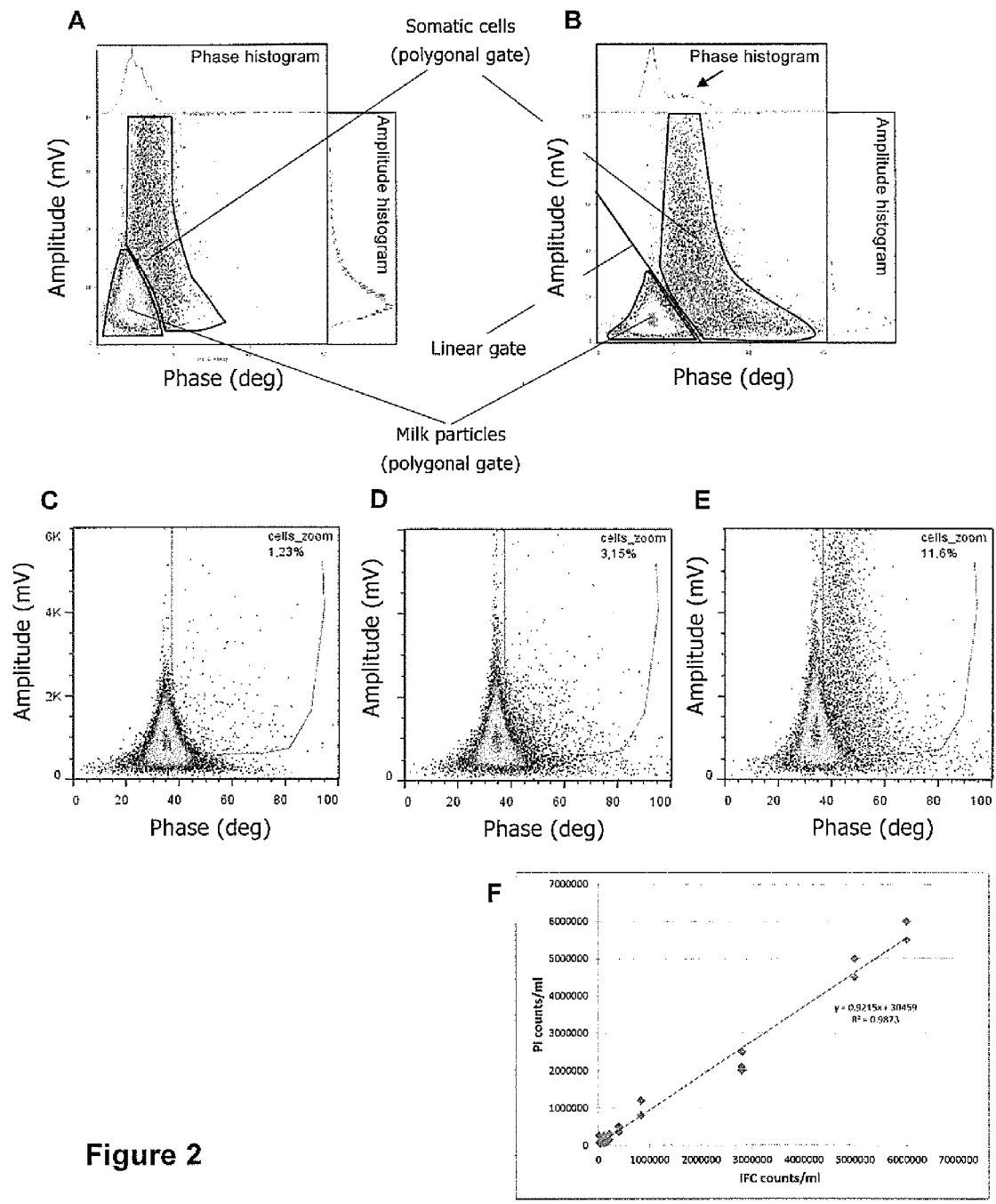
FIG. 2A shows the analysis of raw milk performed at 0.5 MHz.
FIG. 2B the same sample used in FIG. 2A measured at 10 MHz.
FIG. 2C shows the analysis of uninfected milk (33,000 cells/ml)
FIG. 2D shows the analysis of slightly infected milk (390,000 cells/ml)
FIG. 2E shows the analysis of highly infected milk (840,000 cells/ml)
FIG. 2F shows the correlation between the SCC performed by impedance flow cytometry and optical counting performed after cell labelling with PI (propidium iodide)

As opposed to conventional impedance analysis performed with Coulter counters, not only the Amplitude of the signal is recorded, but also the Phase φ. Triggering against the real part of the impedance signals and plotting them on a Phase-Amplitude diagram, in which each dot represents the signal of one single cell or milk particle, leads to the data depicted in FIG. 2. The dot plots are complemented with the relative histograms (Amplitude for y-axis, Phase for x-axis). FIG. 2A shows the analysis of raw milk performed at 0.5 MHz and FIG. 2B the same sample with the same particles and cells measured at 10 MHz. The discrimination of milk particles and somatic cells is as expected more distinct at 10 MHz than at lower frequencies (arrow in FIG. 2B indicates somatic cell population). The main differentiation parameter is the phase angle of the impedance signal, a parameter that is not determined with conventional Coulter counters. By increasing the bandwidth of the electronics a better discrimination can be achieved with measurements at higher frequencies (up to 30 MHz) and thus full separation of particles and cells without the need of any calibration prior to analysis can be obtained.

With the use of commercially available software tools, the somatic cell population can be easily gated out with linear or polygonal functions, separated from the milk particles and counted, as shown in FIG. 2B. FIGS. 2C to 2E provide further evidence that the discrimination of milk particles from somatic cells is achievable with the selection of appropriate gating functions, which supply cell counts comparable to those obtained with conventional or more complex, optical state-of-the-art technologies. FIG. 2F shows such a correlation by comparing SSC determined by impedance flow cytometry (IFC) and using DNA labelling dyes (PI=propidium iodide) and subsequent optical counting using a microspcope. Alternatively, triggering can directly occur as mentioned above using a specific formula combining the measured impedance values.

Figure 3:
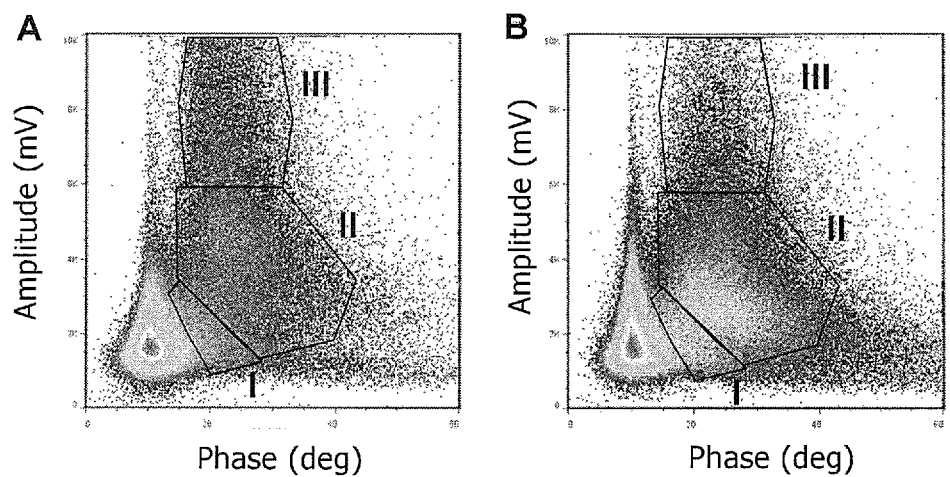
FIG. 3 shows the outcome of an analysis for raw milk diagnosing the status of a mastitis infection of two infected cows.

According to this invention the method allows for diagnosing the status of a mastitis infection directly after milking according to the analysis of the SCC. FIG. 3 shows the outcome of such an analysis for raw milk of two infected cows. For this purpose a larger sample of raw milk is analysed (about 50,000 to 100,000 cells). Again, before passing the sample through the micro fluidic device, it is first filtered with a 15-30 μm. Triggering occurs as described above. Impedance analysis of raw milk using the described method allows for further differentiation of somatic cell sub-populations, consisting mainly of lymphocytes (I), granulocytes (II) and monocytes/macrophages (III). These cell types show differences in their signal amplitudes (reflecting size), but also in their signal phase information. The latter is an important criterion for the differentiation of lymphocytes and granulocytes, which have overlapping dimensions. It is generally known that the first reaction to an infection leads to an increase of granulocytes, followed in a later stage by an increase of monocytes/macrophages. The examples in FIG. 3 show the raw milk analysis of two different cows with mastitis, FIG. 3A revealing the milk of a cow with a late infection according to the high count of macrophages, and FIG. 3B representing the milk of a cow in an earlier infection stage due to its high count of granulocytes. Thus, this cow-site method provides the opportunity for a veterinary doctor to determine the relative ratio of the somatic cell sub-populations and therefore to rapidly assess the infection status of a mastitis as well as to monitor the effects of therapies, and consequently to take at-site decisions instead of waiting for long-lasting analyses in his or other analytical laboratories.

The fact that the impedance value of raw milk can vary as a consequence of its SCC, but also from other natural constituents of milk (fat content, urea, lactose, water, etc.), can impinge on the need for automation in a routine process. In order to use reliable trigger and gating parameters for the determination of the SCC as well as of its sub-populations, an internal calibration of the impedance value becomes necessary. Usually, the adjustment is minimal and can be done as soon as raw milk flows through the micro fluidic chip. The extent of this adjustment can be considered in analogy to the absolute impedance value of the liquid as a preliminary indication of the SCC. The internal calibration can also compensate potential chip-to-chip variations, which might become evident when the chips need to be replaced during a routine analysis.

As SCC increases normally in response to pathogenic bacteria, it is also important to quantify the bacterial cell count (BCC) in raw milk. Bacterial infections result from external contaminations, such as scarce cleaning of the milk transport equipment or of the cow's teats prior to milking. Accepted BCC values for human consumption vary from country to country and range from 100,000 to 1,000,000 cells/ml. Nowadays, BCC is not determined at the production site, because its requirement of a well-equipped laboratory instrumentation. Optical imaging instruments fail because of the rather small cell dimensions (around 1 µm). Impedance-based technologies, on the other hand, cannot separate the cells from milk particles. Quantification is therefore performed with expensive flow cytometers in large analytical laboratories, or with conventional plate cultures in laboratories of dairy product manufacturers or veterinary doctors. Usually, therefore, BCC values are available only a few days after milking.

Figure 4:
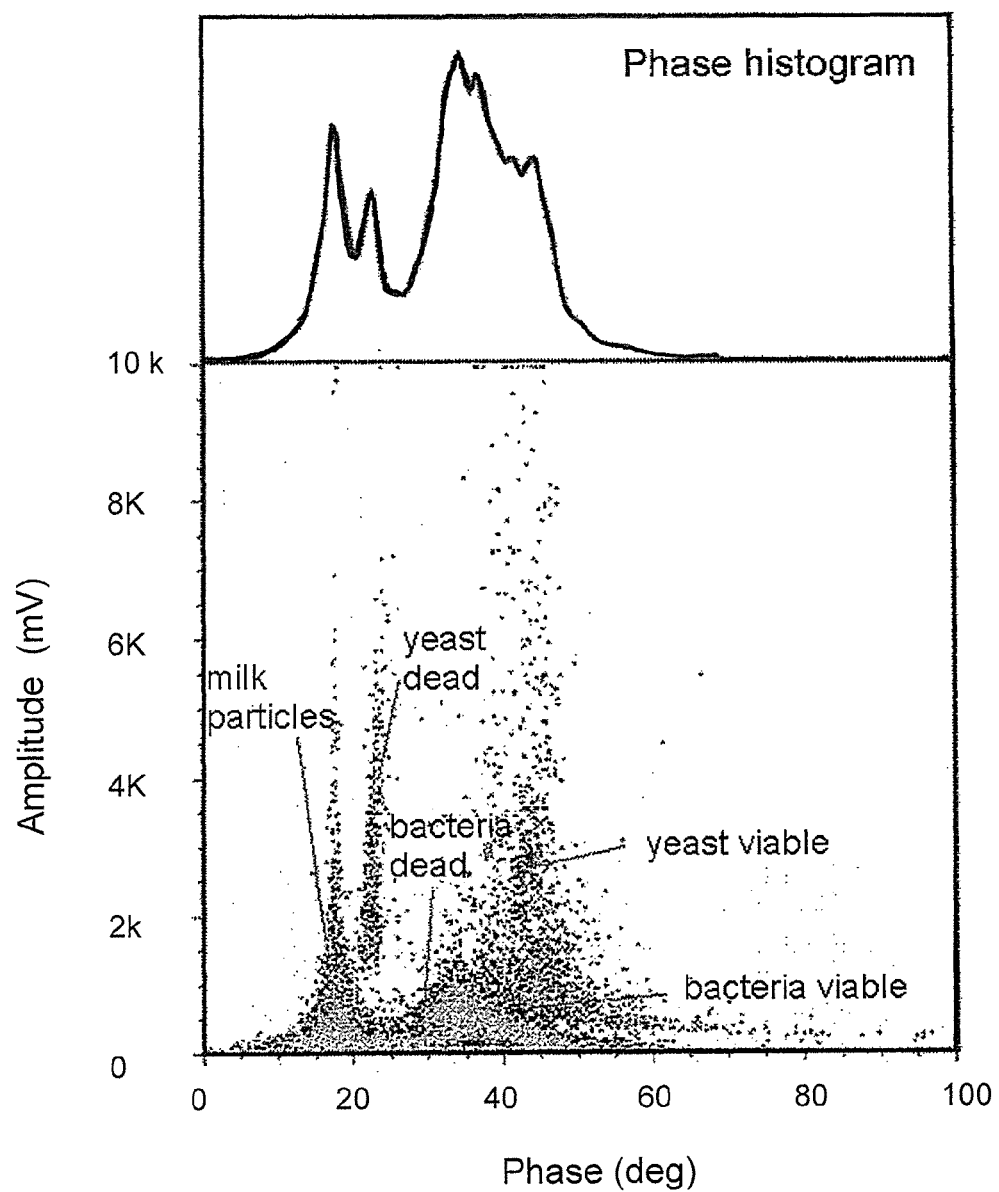
FIG. 4 shows an example of the potential of high-frequency impedance analysis.

Further, this invention allows a fast method for determining the BCC in raw milk directly after milking. Similar to the determination of SCC, raw milk is first filtered using a mesh size of max. 5-10 µm, which will remove large non-cellular particles and a part of the somatic cells. Bacterial cells are then passed through a micro fluidic chip with channel dimensions of 5×5 µm or 10×10 µm for an increased sensitivity of the device, and counted as described above applying the best trigger parameter. FIG. 4 shows an example of the potential of high-frequency impedance analysis. Raw milk was skimmed (centrifugation) in order to better illustrate the resolution of various cell types. To the milk sample, which was 14 days old and quite acidic due to bacterial growth, dead and living yeast cells, as well as dead *Lactobacilli* were added for demonstration purposes. It is clearly visible that bacteria and yeast have higher phase signals than milk particles (as already shown for somatic cells) and that the phase angle of dead cells normally decreases (as shown by David et al. in VIABILITY AND MEMBRANE POTENTIAL ANALYSIS OF *BACILLUS MEGATERIUM* CELLS BY IMPEDANCEFLOW CYTOMETRY, Biotechnology and Bioengineering (2012), 109 (2), 483-492).

Simultaneous SCC and BCC can be achieved by sequential filtering of the milk sample coupled to the measurement with the appropriate chip, for example by filtering first with a 30 µm filter with subsequent analysis using a chip with 20 µm channel dimensions and then, in the same flow, implementing a filtration with a 10 µm filter with subsequent analysis using a chip with 5 µm channel dimensions. Alternatively, the sensitivity (signal-to-noise ratio) of the chip-based impedance analysis can be increased, for example by reducing the bandwidth of the electronics to a smaller frequency range, i.e. from 10 to 20 MHz, which allows for simultaneous analysis of SCC and BCC in a chip with 30 µm channel dimensions and one single filtration step.

Figure 5:
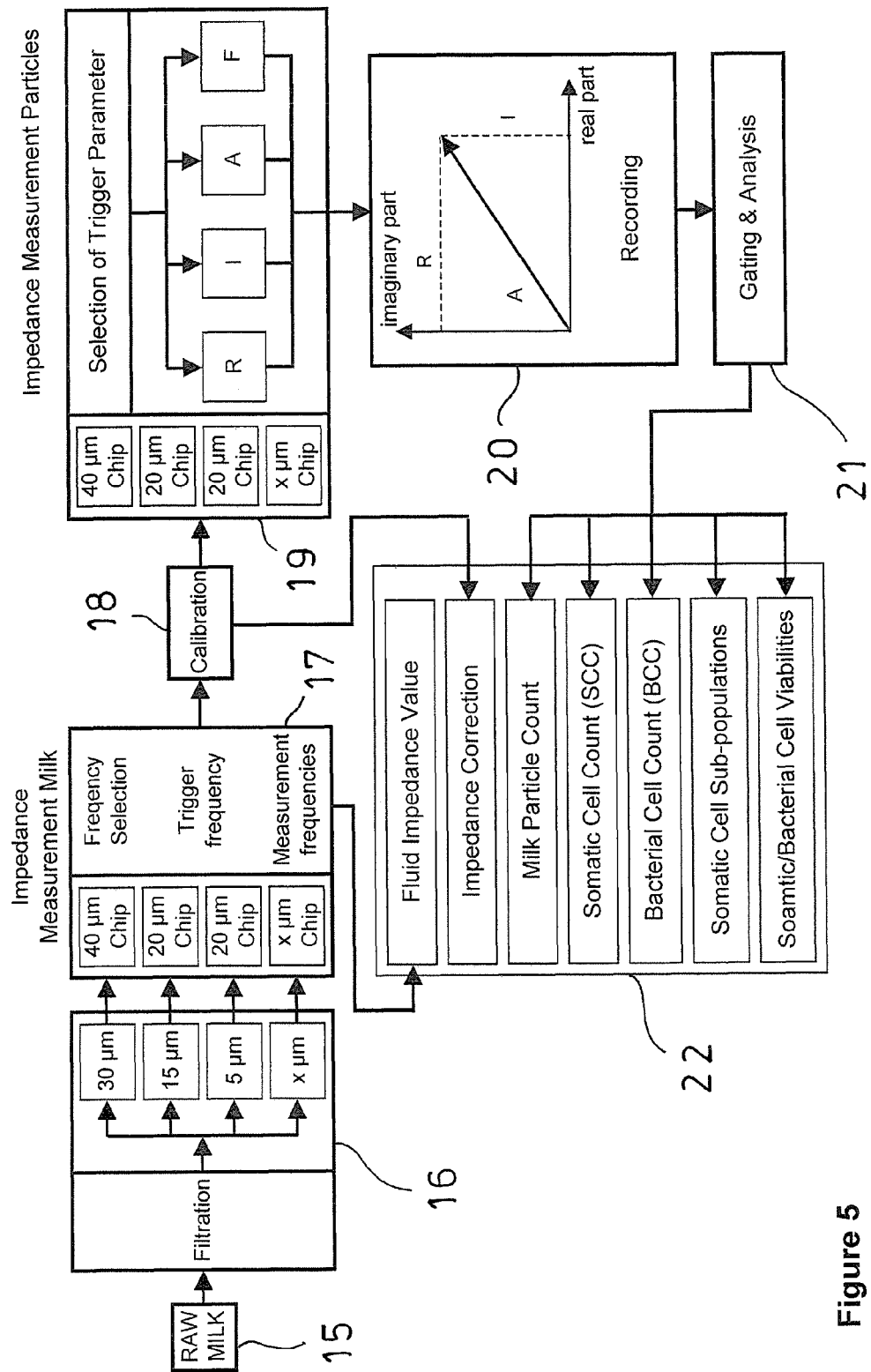
FIG. 5 a block diagram of the method.

In FIG. 5 the principle of the method is depicted in a block diagram. It shows that raw milk is filtered by appropriate filter means 16 having a mesh size depending on the channel size. The mesh size for filtration can be 5, 15, 30 µm or any other appropriate size smaller than the sensing channel of the chip. Subsequently means 17 for impedance measurement of the milk perform a respective measurement by providing respective channels 4 (FIG. 6) being a given amount or percentage larger that the size of the particles passing the filter means 16. The means 17 further comprise means for frequency selection, which chose frequencies for trigger and/or measurement. The trigger frequency is used for calibration with reference numeral 18. The calibration is used for impedance correction depending on the size of the micro channels 4 for impedance measurement of particles as depicted in block 19 and/or depending on the measured fluid impedance. For impedance measurement of the particles a selection of single trigger parameters for the R-, I-, and A-values, or of a trigger formula (F) combining these values and also including the phase value φ of the impedance is performed. The result of the measurement is recorded with respective recording means 20 and then according to respective gating and analysing performed by respective means 21 and completed as shown in block 22. Block 22 includes the results, which can be obtained by the method and apparatus. It comprises the already mentioned fluid impedance values received without using calibration directly after the selection of measurement frequencies in block 17 and the impedance correction after calibration according to block 18. Further, block 22 includes the results of gating and analysis of block 21, which are: milk particle count, SCC, BCC, somatic cell sub-populations, somatic/bacterial cell viabilities.

Figure 6:
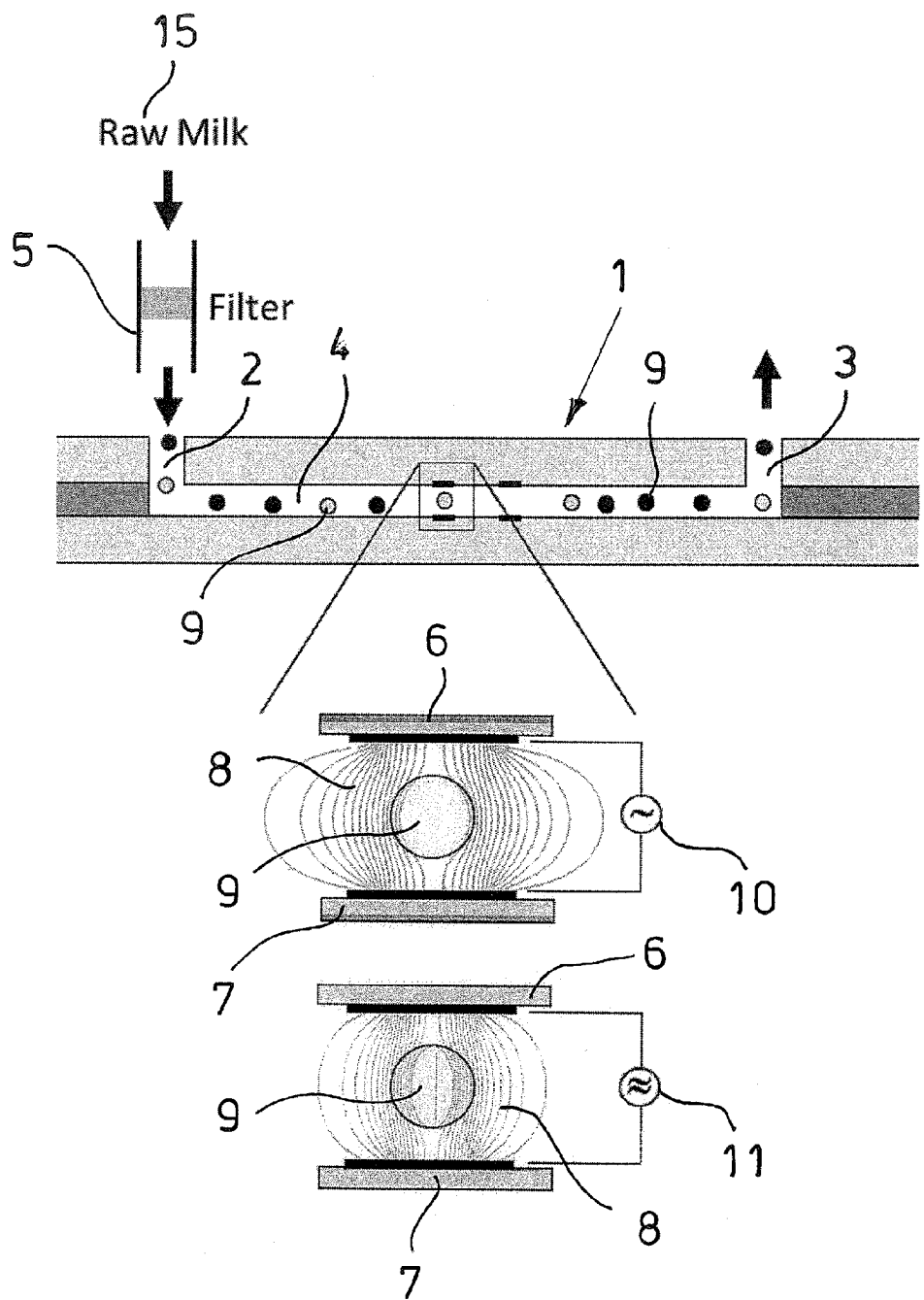
FIG. 6 a principle depiction of a micro fluidic chip with a micro channel and electrodes with the influence of low and high frequency on the particle between the electrodes.

FIG. 6 shows the principle in connection with a chip 1 having an inlet 2 and an outlet 3 with a micro channel 4 there between. A filter 5 is arranged before the inlet 2. The filter 5 can be part of a complete apparatus or a separate device. The mesh size of the filter 5 depends on the size of the particles, which shall be analysed, and the diameter of the micro channel 4. The micro channel 5 comprises electrodes 6 and 7 for generating an electrical AC field 8 in between. Particles 9 of the raw milk pass through the filter 5 into the micro channel 4. Between the electrodes 6 and 7 the particle influences the electrical field and the impedance or the change of the impedance is measured by applying a high frequency voltage 10. FIG. 6 shows the electrical field lines between the electrodes 6 and 7 and a particle 9 between the electrodes 6 and 7. The figure shows the effect of a low-frequency field with numeral 10 and a high-frequency field with numeral 11 on a model cell, whose membrane behaves electrically different at higher frequencies. With the chip single cells can be discriminated from non-cellular milk particles according to the different dielectric properties. In addition, integration of specific trigger parameters can simplify cell discrimination and provide the required automation possibilities needed for a routine-based analysis.

Figure 7:
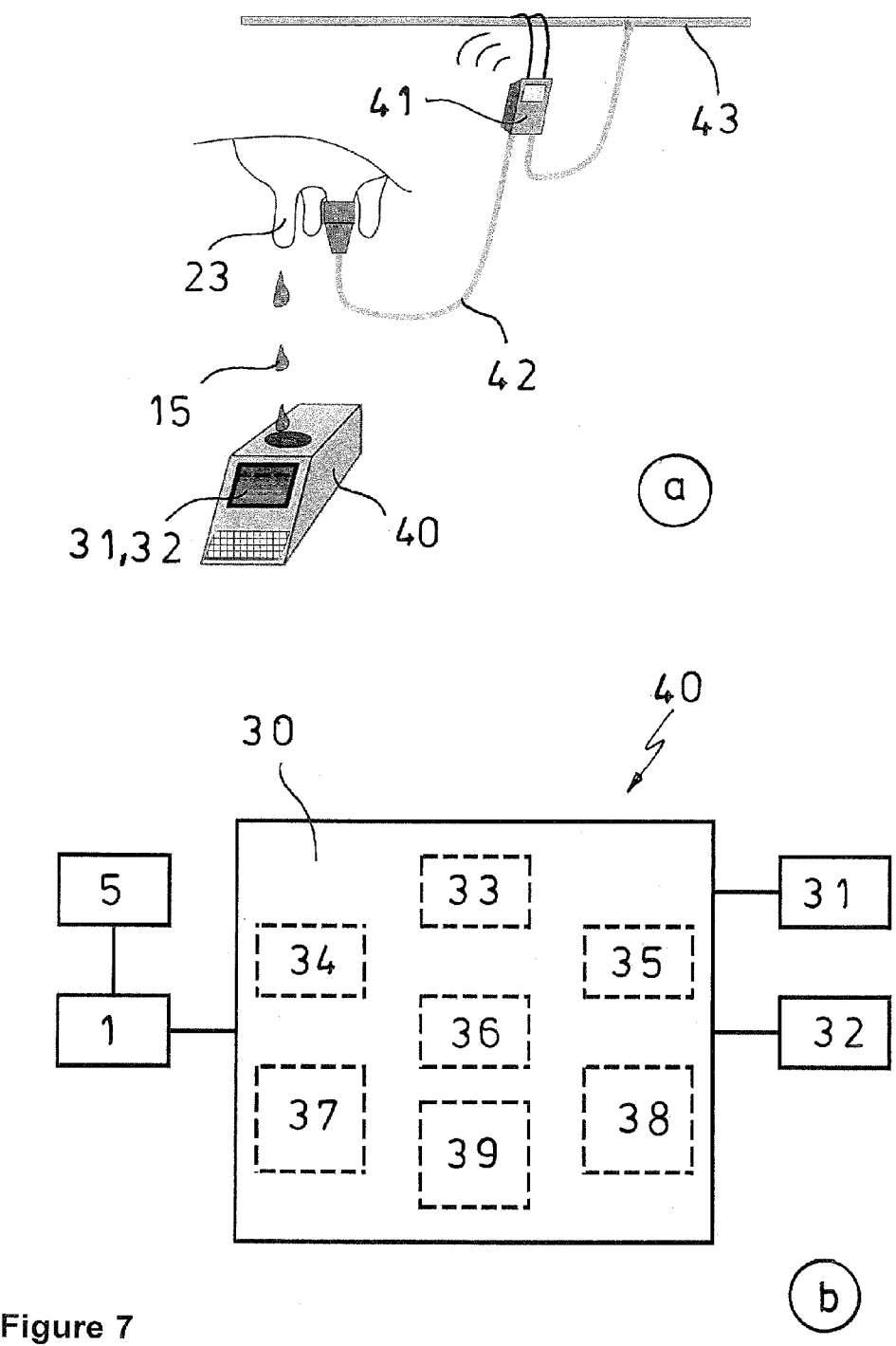
FIG. 7 a measurement principle (FIG. 7A) and a block diagram of the apparatus (FIG. 7B).

FIG. 7A shows the principle arrangement of two measurement possibilities. The apparatus 40 receives a sample of raw milk 15 from the udder of the cow. In the figure that is exemplarily depicted only with drops. The apparatus has a touch screen, which serves as input means of 32 and monitoring means 33. The other possibility is to analyse directly the raw milk from the udder 23 during its way via conduits 42 to the pipeline 43 of a milking plant. The result of the analysis here is transmitted by a mobile analysis unit 41 to the farmer's control station for further data handling. FIG. 7B shows a block diagram of the elements of the apparatus for forming the method as explained above for the automatic real-time determination and analysis of milk of any animal comprising. A filter 5 is necessary to avoid clogging of the micro channels of the micro fluidic device 1 of FIG. 6, however, the filter may be a part of the apparatus 40 or a separate component. The apparatus 40 comprises besides the micro fluidic device 1 as described in connection with FIG. 6 control means 30 for generating a high frequency voltage at the electrodes 6, 7 and measuring the impedance between the electrodes 6, 7 with and without particles 9 between the electrodes 6, 7. Further, there are input 32 and monitoring 31 means. The control means 30 comprise means 33 being adapted to determine the impedance value of the milk and to calibrate the micro fluidic device on said impedance value, if necessary, means 34 being adapted to count the particles and measure the impedance of the particles, means 35 to determine a trigger parameter for noise extraction and particle recognition, respectively, means 36 being adapted to determine a trigger parameter for discrimination of cells from non-cellular milk particles, means 37 being adapted to analyse the impedance values depending on the amplitude values and the phase angle values, and means 38 being adapted to select the cells and/or non-cellular milk particles according their amplitude and/or phase angle values. Further included are means 39 being adapted to determinate the impedance value of the analysed milk, and/or to determinate the somatic cell sub-populations, and/or to determinate the milk particle content, and/or to determinate the viability of somatic or bacterial cells.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. A method for automatic discrimination and enumeration of particles including cells and non-cellular milk particles in raw milk using high-frequency impedance measurements in a range between 0.1 and 30 MHz in a micro fluidic device, comprising:
- passing of raw milk through a filter to avoid clogging of the micro fluidic device;
- determining an impedance value of the milk and calibrating the micro fluidic device on said impedance value, if necessary,
- counting the particles and measuring impedance components of each particle;
- determining from one of these components a trigger level suitable for noise extraction and particle recognition, respectively;
- determining from one impedance component a trigger level for discrimination of cells from non-cellular milk particles;
- analysing the impedance components depending on amplitude values and phase angle values; and
- discriminating and enumerating the cells and/or non-cellular milk particles according their amplitude and/or phase angle values.

2. The method according to claim 1, comprising analysing somatic cells.

3. The method according to claim 1, comprising analysing bacterial cells.

4. The method according to claim 1, comprising a simultaneous somatic cell count (SCC) and a bacterial cell count (BCC).

5. The method according to claim 1, comprising a determination of the impedance value of the analysed milk, and/or a determination of the somatic cell sub-populations, and/or a determination of the content of fat globules, and/or a determination of the viability of somatic or bacterial cells.

* * * * *